United States Patent
Howell

(10) Patent No.: US 11,890,429 B2
(45) Date of Patent: Feb. 6, 2024

(54) RAPIDLY INSERTED CENTRAL CATHETER AND METHODS THEREOF

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 107 days.

(21) Appl. No.: 17/006,553

(22) Filed: Aug. 28, 2020

(65) Prior Publication Data

US 2021/0069471 A1   Mar. 11, 2021

Related U.S. Application Data

(60) Provisional application No. 62/898,408, filed on Sep. 10, 2019.

(51) Int. Cl.
   *A61M 25/01*   (2006.01)
   *A61M 25/09*   (2006.01)
   *A61M 25/00*   (2006.01)

(52) U.S. Cl.
   CPC .... *A61M 25/0105* (2013.01); *A61M 25/0009* (2013.01); *A61M 25/09* (2013.01); *A61M 2025/09158* (2013.01)

(58) Field of Classification Search
   CPC .......... A61M 25/0043; A61M 25/0105; A61M 25/0009; A61M 25/001; A61M 25/0068;
   (Continued)

(56) References Cited

U.S. PATENT DOCUMENTS

| 1,013,691 A | 1/1912 | Shields |
| 3,225,762 A | 12/1965 | Guttman |

(Continued)

FOREIGN PATENT DOCUMENTS

| EP | 0730880 A1 | 9/1996 |
| EP | 2061385 A1 | 5/2009 |

(Continued)

OTHER PUBLICATIONS

U.S. Appl. No. 15/008,628, filed Jan. 28, 2016 Final Office Action dated May 30, 2018.

(Continued)

*Primary Examiner* — Tiffany Legette
(74) *Attorney, Agent, or Firm* — Rutan & Tucker LLP

(57) ABSTRACT

Rapidly inserted central catheters ("RICC"), and methods thereof. A RICC can include a catheter tube including a first section in a distal-end portion of the catheter tube, a second section in the distal-end portion of the catheter tube proximal of the first section, and a junction between the first and second sections of the catheter tube. The first section of the catheter tube can be formed of a first material having a first durometer. The second section of the catheter tube can be formed of a second material having a second durometer less than the first durometer. The first and second sections of the catheter tube can have a column strength sufficient to prevent buckling of the catheter tube when inserted into an insertion site and advanced through a vasculature of a patient.

24 Claims, 7 Drawing Sheets

(58) Field of Classification Search
CPC .............. A61M 25/0008; A61M 25/09; A61M 2025/0059; A61M 2025/09158; A61M 25/0054
See application file for complete search history.

(56) References Cited

U.S. PATENT DOCUMENTS

| | | |
|---|---|---|
| 3,890,976 A | 6/1975 | Bazell et al. |
| 4,205,675 A | 6/1980 | Vaillancourt |
| 4,270,535 A | 6/1981 | Bogue et al. |
| 4,292,970 A | 10/1981 | Hession, Jr. |
| 4,468,224 A | 8/1984 | Enzmann et al. |
| 4,525,157 A | 6/1985 | Vaillancourt |
| 4,581,019 A | 4/1986 | Curelaru et al. |
| 4,661,300 A | 4/1987 | Daugherty |
| 5,017,259 A | 5/1991 | Kohsai |
| 5,040,548 A | 8/1991 | Yock |
| 5,057,073 A | 10/1991 | Martin |
| 5,112,312 A | 5/1992 | Luther |
| 5,120,317 A | 6/1992 | Luther |
| 5,188,593 A | 2/1993 | Martin |
| 5,195,962 A | 3/1993 | Martin et al. |
| 5,207,650 A | 5/1993 | Martin |
| 5,267,958 A | 12/1993 | Buchbinder et al. |
| 5,295,970 A | 3/1994 | Clinton et al. |
| 5,306,247 A | 4/1994 | Pfenninger |
| 5,328,472 A | 7/1994 | Steinke et al. |
| 5,350,358 A | 9/1994 | Martin |
| 5,368,567 A | 11/1994 | Lee |
| 5,378,230 A | 1/1995 | Mahurkar |
| 5,380,290 A | 1/1995 | Makower et al. |
| 5,389,087 A | 2/1995 | Miraki |
| 5,439,449 A | 8/1995 | Mapes et al. |
| 5,443,457 A | 8/1995 | Ginn et al. |
| 5,489,271 A | 2/1996 | Andersen |
| 5,573,520 A | 11/1996 | Schwartz et al. |
| 5,683,370 A | 11/1997 | Luther et al. |
| 5,690,613 A | 11/1997 | Verbeek |
| 5,718,678 A | 2/1998 | Fleming, III |
| 5,772,636 A | 6/1998 | Brimhall et al. |
| 5,885,251 A | 3/1999 | Luther |
| 5,919,164 A | 7/1999 | Andersen |
| 5,947,940 A | 9/1999 | Beisel |
| 5,957,893 A | 9/1999 | Luther et al. |
| 6,206,849 B1 | 3/2001 | Martin et al. |
| 6,332,877 B1 | 12/2001 | Michels |
| 6,475,187 B1 | 11/2002 | Gerberding |
| 6,606,515 B1 | 8/2003 | Windheuser et al. |
| 6,716,228 B2 | 4/2004 | Tal |
| 6,726,659 B1 | 4/2004 | Stocking et al. |
| 6,819,951 B2 | 11/2004 | Patel et al. |
| 6,821,287 B1 | 11/2004 | Jang |
| 6,926,692 B2 | 8/2005 | Katoh et al. |
| 6,962,575 B2 | 11/2005 | Tal |
| 6,994,693 B2 | 2/2006 | Tal |
| 6,999,809 B2 | 2/2006 | Currier et al. |
| 7,025,746 B2 | 4/2006 | Tal |
| 7,029,467 B2 | 4/2006 | Currier et al. |
| 7,037,293 B2 | 5/2006 | Carrillo et al. |
| 7,074,231 B2 | 7/2006 | Jang |
| 7,141,050 B2 | 11/2006 | Deal et al. |
| 7,144,386 B2 | 12/2006 | Korkor et al. |
| 7,311,697 B2 | 12/2007 | Osborne |
| 7,364,566 B2 | 4/2008 | Elkins et al. |
| 7,377,910 B2 | 5/2008 | Katoh et al. |
| 7,390,323 B2 | 6/2008 | Jang |
| D600,793 S | 9/2009 | Bierman et al. |
| D601,242 S | 9/2009 | Bierman et al. |
| D601,243 S | 9/2009 | Bierman et al. |
| 7,594,911 B2 | 9/2009 | Powers et al. |
| 7,691,093 B2 | 4/2010 | Brimhall |
| 7,722,567 B2 | 5/2010 | Tal |
| D617,893 S | 6/2010 | Bierman et al. |
| D624,643 S | 9/2010 | Bierman et al. |
| 7,819,889 B2 | 10/2010 | Healy et al. |
| 7,857,788 B2 | 12/2010 | Racz |
| D630,729 S | 1/2011 | Bierman et al. |
| 7,909,797 B2 | 3/2011 | Kennedy, II et al. |
| 7,909,811 B2 | 3/2011 | Agro et al. |
| 7,922,696 B2 | 4/2011 | Tal et al. |
| 7,938,820 B2 | 5/2011 | Webster et al. |
| 7,967,834 B2 | 6/2011 | Tal et al. |
| 7,985,204 B2 | 7/2011 | Katoh et al. |
| 8,073,517 B1 | 12/2011 | Burchman |
| 8,105,286 B2 | 1/2012 | Anderson et al. |
| 8,192,402 B2 | 6/2012 | Anderson et al. |
| 8,202,251 B2 | 6/2012 | Bierman et al. |
| 8,206,356 B2 | 6/2012 | Katoh et al. |
| 8,372,107 B2 | 2/2013 | Tupper |
| 8,377,006 B2 | 2/2013 | Tal et al. |
| 8,454,577 B2 | 6/2013 | Joergensen et al. |
| 8,585,858 B2 | 11/2013 | Kronfeld et al. |
| 8,657,790 B2 | 2/2014 | Tal et al. |
| 8,672,888 B2 | 3/2014 | Tal |
| 8,696,645 B2 | 4/2014 | Tal et al. |
| 8,784,362 B2 | 7/2014 | Boutilette et al. |
| 8,827,958 B2 | 9/2014 | Bierman et al. |
| 8,876,704 B2 | 11/2014 | Golden et al. |
| 8,882,713 B1 | 11/2014 | Call et al. |
| 8,900,192 B2 | 12/2014 | Anderson et al. |
| 8,900,207 B2 | 12/2014 | Uretsky |
| 8,915,884 B2 | 12/2014 | Tal et al. |
| 8,956,327 B2 | 2/2015 | Bierman et al. |
| 9,023,093 B2 | 5/2015 | Pal |
| 9,138,252 B2 | 9/2015 | Bierman et al. |
| 9,180,275 B2 | 11/2015 | Helm |
| 9,265,920 B2 | 2/2016 | Rundquist et al. |
| 9,272,121 B2 | 3/2016 | Piccagli |
| 9,522,254 B2 | 12/2016 | Belson |
| 9,554,785 B2 | 1/2017 | Walters et al. |
| 9,566,087 B2 | 2/2017 | Bierman et al. |
| 9,675,784 B2 | 6/2017 | Belson |
| 9,713,695 B2 | 7/2017 | Bunch et al. |
| 9,764,117 B2 | 9/2017 | Bierman et al. |
| 9,770,573 B2 | 9/2017 | Golden et al. |
| 9,814,861 B2 | 11/2017 | Boutilette et al. |
| 9,820,845 B2 | 11/2017 | von Lehe et al. |
| 9,861,383 B2 | 1/2018 | Clark |
| 9,884,169 B2 | 2/2018 | Bierman et al. |
| 9,889,275 B2 | 2/2018 | Voss et al. |
| 9,913,585 B2 | 3/2018 | McCaffrey et al. |
| 9,913,962 B2 | 3/2018 | Tal et al. |
| 9,950,139 B2 | 4/2018 | Blanchard et al. |
| 9,981,113 B2 | 5/2018 | Bierman |
| 10,010,312 B2 | 7/2018 | Tegels |
| 10,065,020 B2 | 9/2018 | Gaur |
| 10,098,724 B2 | 10/2018 | Adams et al. |
| 10,111,683 B2 | 10/2018 | Tsamir et al. |
| 10,118,020 B2 | 11/2018 | Avneri et al. |
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 | 8/2019 | Mitchell et al. |
| 10,675,440 B2 | 6/2020 | Abitabilo et al. |
| 10,806,901 B2 | 10/2020 | Burkholz et al. |
| 2001/0044594 A1 | 11/2001 | Martin et al. |
| 2002/0040231 A1 | 4/2002 | Wysoki |
| 2002/0198492 A1* | 12/2002 | Miller .............. A61M 25/1027 604/96.01 |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0116901 A1 | 6/2004 | Appling |
| 2004/0193093 A1 | 9/2004 | Desmond |
| 2004/0230178 A1* | 11/2004 | Wu ................ A61B 17/320725 604/527 |
| 2005/0004554 A1 | 1/2005 | Osborne |
| 2005/0245882 A1 | 11/2005 | Elkins et al. |
| 2005/0283221 A1 | 12/2005 | Mann et al. |

(56) References Cited

U.S. PATENT DOCUMENTS

| | | |
|---|---|---|
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2008/0045894 A1 | 2/2008 | Perchik et al. |
| 2008/0125744 A1 | 5/2008 | Treacy |
| 2008/0125748 A1 | 5/2008 | Patel |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2009/0221961 A1 | 9/2009 | Tal et al. |
| 2009/0270889 A1 | 10/2009 | Tal et al. |
| 2010/0256487 A1 | 10/2010 | Hawkins et al. |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0220942 A1 | 8/2012 | Hall et al. |
| 2012/0283640 A1 | 11/2012 | Anderson et al. |
| 2012/0316500 A1 | 12/2012 | Bierman et al. |
| 2013/0012924 A1 | 1/2013 | Davis et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094741 A1 | 4/2014 | Bellisario et al. |
| 2014/0100552 A1 | 4/2014 | Gallacher et al. |
| 2014/0180255 A1 | 6/2014 | LeBlanc et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0080939 A1 | 3/2015 | Adams et al. |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0220786 A1 | 8/2016 | Mitchell et al. |
| 2016/0325073 A1 | 11/2016 | Davies et al. |
| 2016/0338728 A1 | 11/2016 | Tal |
| 2016/0346503 A1* | 12/2016 | Jackson ............ A61M 25/0045 |
| 2017/0035989 A1 | 2/2017 | Gilman |
| 2017/0035990 A1 | 2/2017 | Swift |
| 2017/0072165 A1* | 3/2017 | Lim ............ A61M 25/0045 |
| 2017/0128700 A1 | 5/2017 | Roche Rebollo |
| 2017/0172653 A1 | 6/2017 | Urbanski et al. |
| 2017/0239443 A1 | 8/2017 | Abitabilo et al. |
| 2017/0273713 A1 | 9/2017 | Shah et al. |
| 2017/0326339 A1 | 11/2017 | Bailey et al. |
| 2017/0361070 A1 | 12/2017 | Hivert |
| 2018/0021545 A1 | 1/2018 | Mitchell et al. |
| 2018/0116690 A1* | 5/2018 | Sarabia ............ A61M 25/09 |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0193042 A1 | 7/2018 | Wilson et al. |
| 2018/0296799 A1 | 10/2018 | Horst et al. |
| 2018/0296804 A1 | 10/2018 | Bierman |
| 2019/0015646 A1 | 1/2019 | Matlock et al. |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0255294 A1 | 8/2019 | Mitchell et al. |
| 2019/0276268 A1 | 9/2019 | Akingba |
| 2019/0321590 A1 | 10/2019 | Burkholz et al. |
| 2020/0016374 A1 | 1/2020 | Burkholz et al. |
| 2021/0121661 A1 | 4/2021 | Howell |
| 2021/0121667 A1 | 4/2021 | Howell |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2023/0126869 A1 | 4/2023 | Sepulveda et al. |
| 2023/0132903 A1 | 5/2023 | Sepulveda et al. |
| 2023/0233796 A1 | 7/2023 | Howell |
| 2023/0233800 A1 | 7/2023 | Howell et al. |

FOREIGN PATENT DOCUMENTS

| | | |
|---|---|---|
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3093038 B1 | 5/2019 |
| EP | 2260897 B1 | 9/2019 |
| GB | 1273547 A | 5/1972 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 2003008020 A1 | 1/2003 |
| WO | 2003057272 A2 | 7/2003 |
| WO | 2003066125 A2 | 8/2003 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012162677 A1 | 11/2012 |

(56) References Cited

FOREIGN PATENT DOCUMENTS

| | | |
|---|---|---|
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/146026 A1 | 8/2019 |
| WO | 2019199734 A1 | 10/2019 |
| WO | 2020069395 A1 | 4/2020 |
| WO | 2021050302 A1 | 3/2021 |
| WO | 2021/062023 A1 | 4/2021 |
| WO | 2021/077103 A1 | 4/2021 |
| WO | 2021081205 A1 | 4/2021 |
| WO | 2021086793 A1 | 5/2021 |
| WO | 2023069553 A2 | 4/2023 |
| WO | 2023081314 A1 | 5/2023 |

OTHER PUBLICATIONS

U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 16/398,020, filed Apr. 29, 2019 Final Office Action dated Jan. 25, 2022.
PCT/US2020/057397 filed Oct. 26, 2020 International Search Report and Written Opinion dated Mar. 10, 2021.
U.S. Appl. No. 16/398,020, filed Apr. 29, 2019 Non-Final Office Action dated May 11, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2021/014700 filed Jan. 22, 2021 International Search Report and Written Opinion dated Jun. 29, 2021.
PCT/US2021/039084 filed Jun. 25, 2021 International Search Report and Written Opinion dated Jan. 10, 2022.
U.S. Appl. No. 17/077,728, filed Oct. 22, 2020 Non-Final Office Action dated Feb. 9, 2022.
PCT/US2022/047179 filed Oct. 19, 2022 International Search Report and Written Opinion dated Apr. 18, 2023.
PCT/US2022/048881 filed Nov. 3, 2022 International Search Report and Written Opinion dated Mar. 31, 2023.
PCT/US2023/010971 filed Jan. 17, 2023 International Search Report and Written Opinion dated Jul. 28, 2023.
PCT/US2023/010972 filed Jan. 17, 2023 International Search Report and Written Opinion dated May 30, 2023.
Yamada, T. et al., "Selective Hemi-Portocaval Shunt Based on Portal Vein Pressure for Small-for-Size Graft in Adult Living Donor Liver Transplantation." American Journal of Transplantation, Blackwell Munksgaard, DK, vol. 8, no. 4, Feb. 5, 2008 [Feb. 5, 2008] pp. 847-853.
EP 20862936.0 filed Mar. 28, 2022 Extended European Search Report dated Sep. 19, 2023.

* cited by examiner

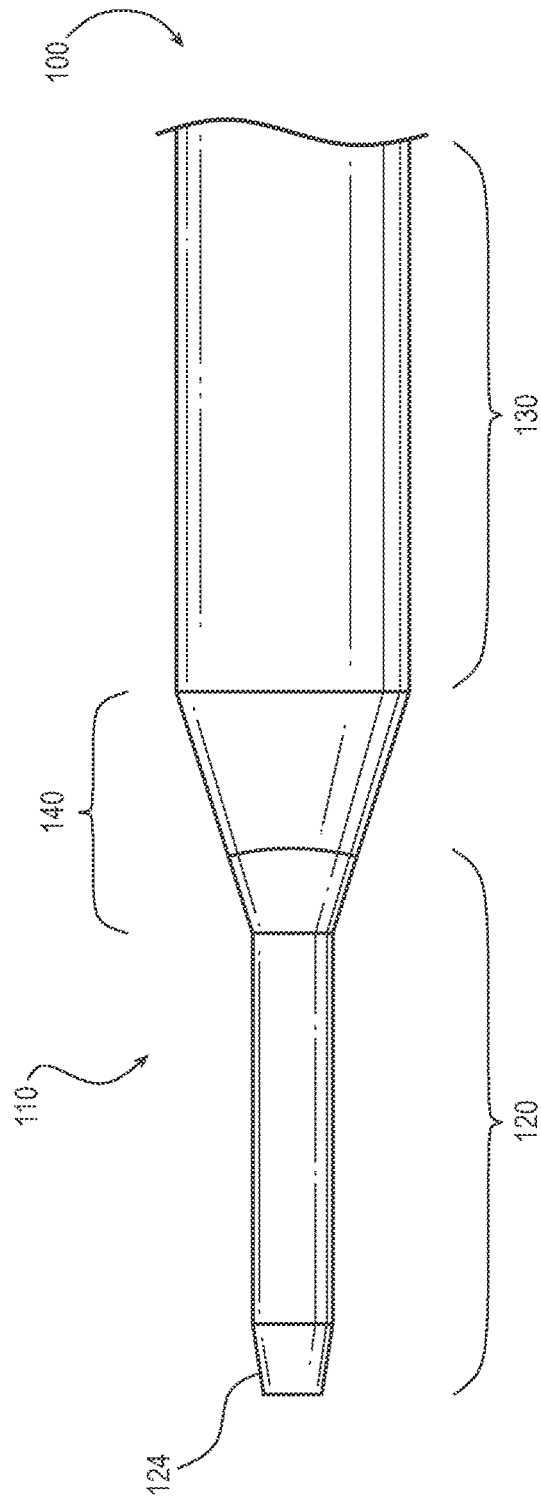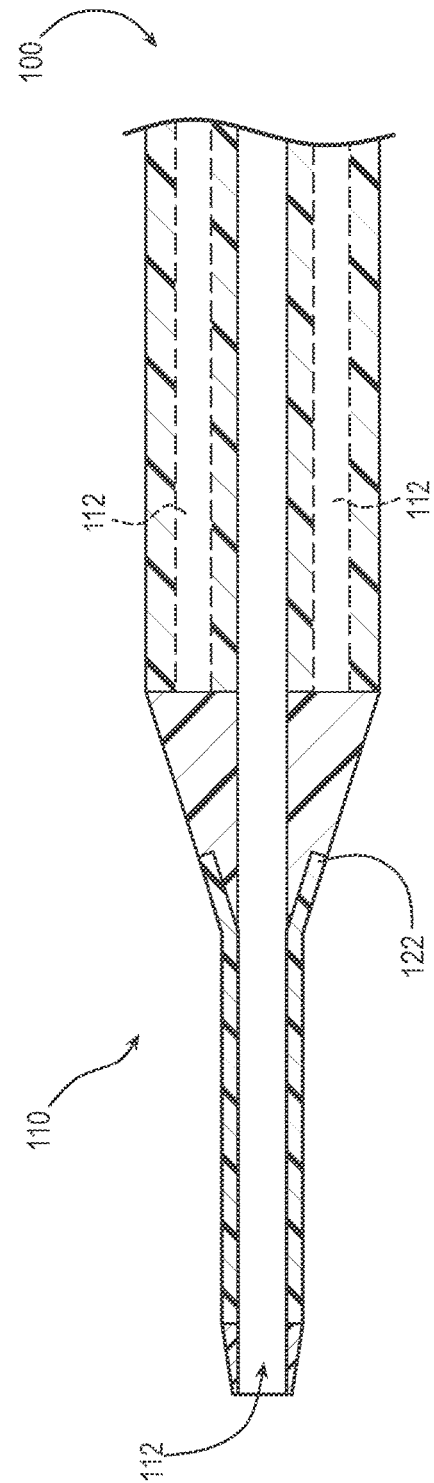
FIG. 1A
FIG. 1B

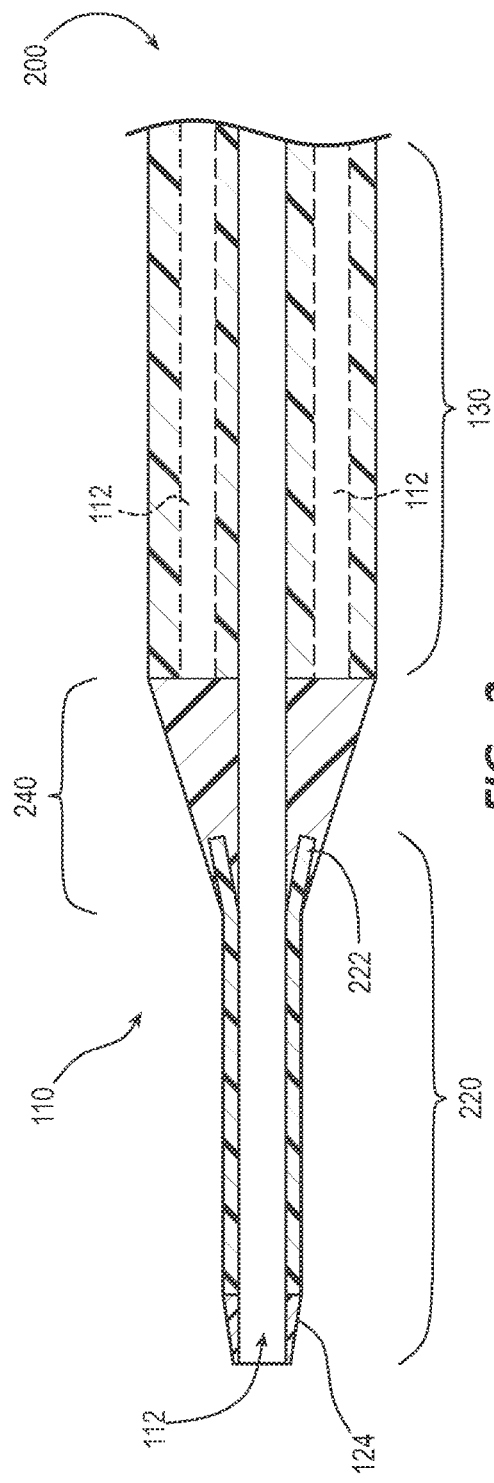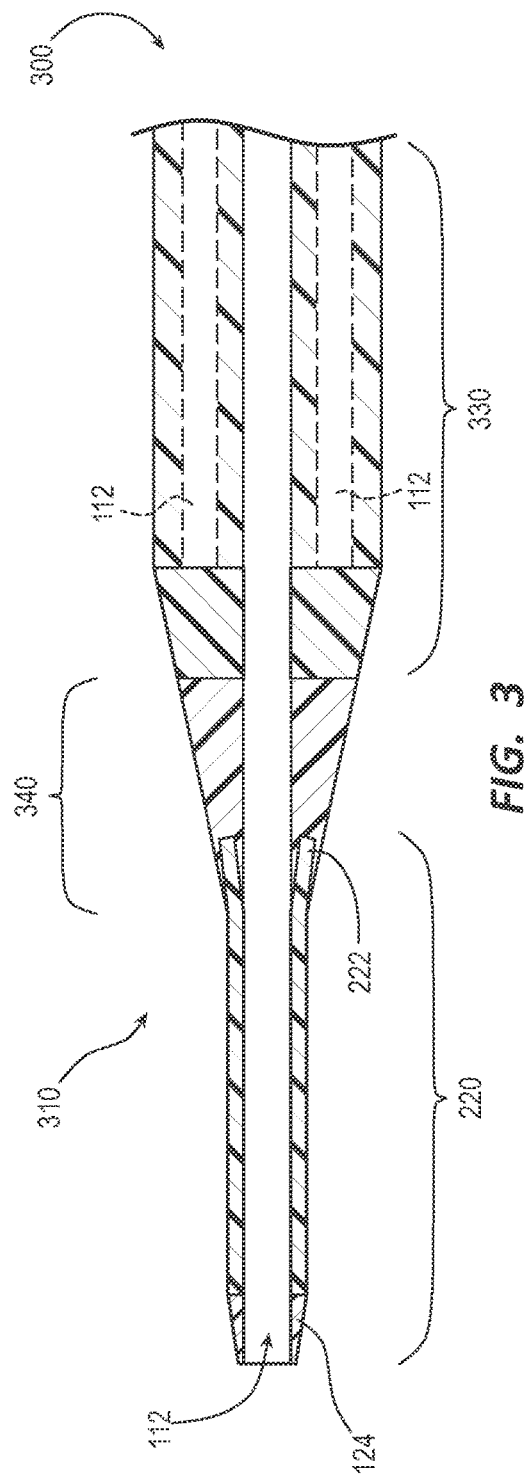

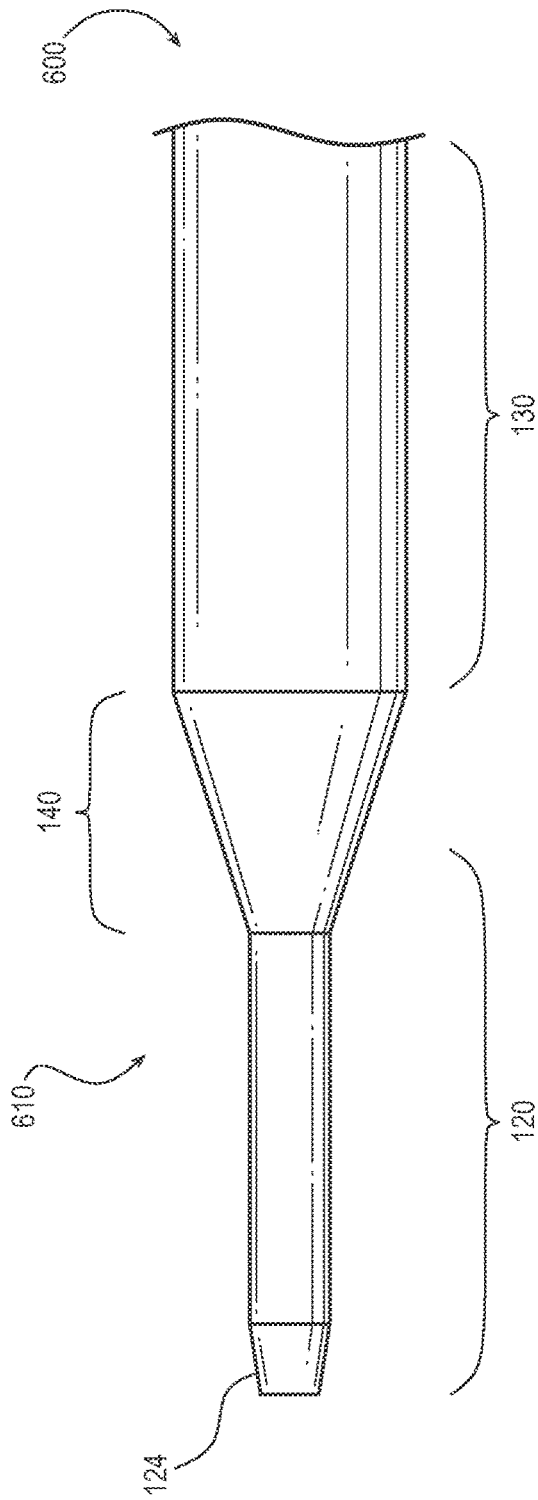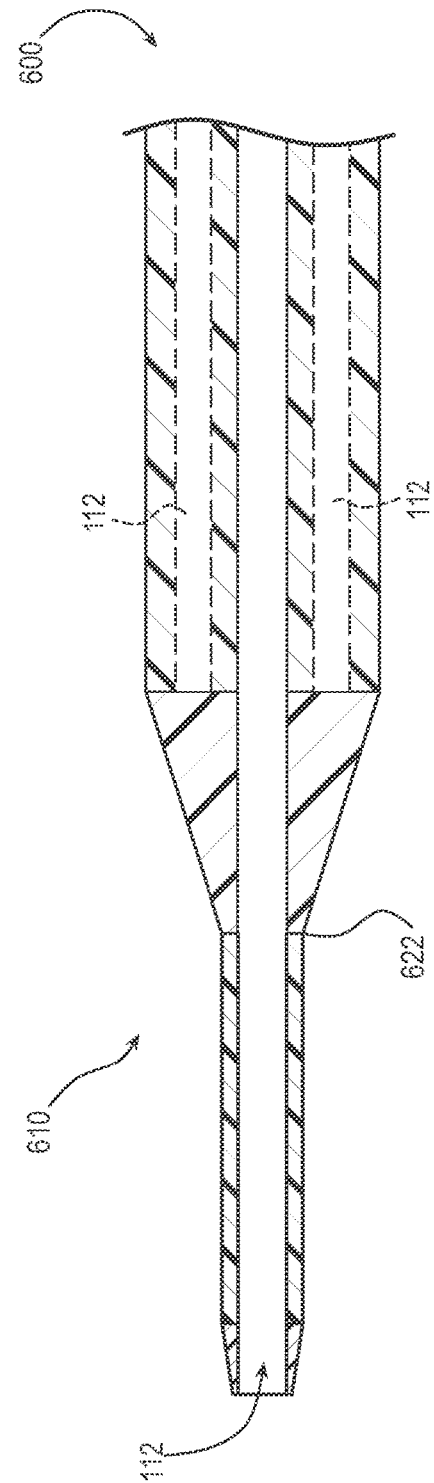

RAPIDLY INSERTED CENTRAL CATHETER AND METHODS THEREOF

PRIORITY

This application claims the benefit of priority to U.S. Provisional Application No. 62/898,408, filed Sep. 10, 2019, which is incorporated by reference in its entirety into this application.

BACKGROUND

A central venous catheter ("CVC") is formed of a material having a relatively low durometer, which contributes to the CVC having a lack of column strength. Due to the lack of column strength, CVCs are commonly introduced into patients and advanced through vasculatures thereof by way of the Seldinger technique. The Seldinger technique utilizes a number of steps and medical devices (e.g., a needle, a scalpel, a guidewire, an introducer sheath, a dilator, a CVC, etc.). While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter into patient and advancing the catheter through a vasculature thereof.

Disclosed herein are rapidly inserted central catheters ("RICCs") and methods thereof that address the foregoing.

SUMMARY

Disclosed herein is a RICC including, in some embodiments, a catheter tube including a first section in a distal-end portion of the catheter tube, a second section in the distal-end portion of the catheter tube proximal of the first section, and a junction between the first and second sections of the catheter tube. The first section of the catheter tube is formed of a first material having a first durometer. The second section of the catheter tube is formed of a second material having a second durometer less than the first durometer. The first and second sections of the catheter tube have a column strength sufficient to prevent buckling of the catheter tube when inserted into an insertion site and advanced through a vasculature of a patient.

In some embodiments, the junction is a third section of the catheter tube formed of a third material having a third durometer between the first and second durometers.

In some embodiments, the junction includes a tapered distal-end portion, the first section of the catheter tube includes a flared proximal-end portion, and the tapered distal-end portion of the junction sits within the flared proximal-end portion of the first section of the catheter tube.

In some embodiments, the junction includes a proximal-end portion, the second section of the catheter tube includes a distal-end portion, and the proximal-end portion of the junction abuts the distal-end portion of the second section of the catheter tube.

In some embodiments, each section of the first and second sections of the catheter tube is welded to the junction in a heat weld.

In some embodiments, each section of the first and second sections of the catheter tube is welded to the junction in a solvent weld.

In some embodiments, the first section of the catheter tube includes a flared proximal-end portion, the second section of the catheter tube includes a tapered distal-end portion, and the tapered distal-end portion of the second section of the catheter tube sits within the flared proximal-end portion of the first section of the catheter tube.

In some embodiments, each section of the first and second sections of the catheter tube is welded to the other section in a heat weld, thereby forming the junction between the first and second sections of the catheter tube.

In some embodiments, each section of the first and second sections of the catheter tube is welded to the other section in a solvent weld, thereby forming the junction between the first and second sections of the catheter tube.

In some embodiments, the RICC includes a necked-down section about the junction. The necked-down section is configured to provide a smooth transition between the first and second sections of the catheter tube.

In some embodiments, the first section of the catheter tube is polytetrafluoroethylene, polypropylene, or polyurethane.

In some embodiments, the second section of the catheter tube is polyvinyl chloride, polyethylene, polyurethane, or silicone.

Also disclosed herein is a method of making a RICC including, in some embodiments, obtaining steps of obtaining each section of a first section, a second section, and a third section of a catheter tube. The first section of the catheter tube is formed of a first material having a first durometer. The second section of the catheter tube is formed of a second material having a second durometer. The third section of the catheter tube is formed of a third material having a third durometer between the first and second durometers. The method also includes a flaring step of flaring a proximal-end portion of the first section of the catheter tube to form a flared proximal-end portion of the first section of the catheter tube. The method also includes an inserting step of inserting a tapered distal-end portion of the third section of the catheter tube into the flared proximal-end portion of the first section of the catheter tube. The method also includes an abutting step of abutting a distal-end portion of the second section of the catheter tube and a proximal-end portion of the third section of the catheter tube. The method also includes welding steps of welding the first, second, and third sections of the catheter tube together to form a junction of the third material between the first and second sections of the catheter tube.

In some embodiments, a welding step of welding the second and third sections of the catheter tube occurs before the inserting and welding steps of inserting the tapered distal-end portion of the third section of the catheter tube into the flared proximal-end portion of the first section of the catheter tube and welding the first and third sections of the catheter tube together.

In some embodiments, each welding step of the welding steps is independently heat welding or solvent welding.

In some embodiments, the method further includes a tapering step of tapering a non-tapered distal-end portion of the third section of the catheter tube to form the tapered distal-end portion of the third section of the catheter tube.

In some embodiments, the method further includes a necking-down step of necking down the catheter tube to form a necked-down section about the junction. The necked-down section is configured to provide a smooth transition between the first, second, and third sections of the catheter tube.

Also disclosed herein is a method of making a RICC including, in some embodiments, obtaining steps of obtaining a first section of a catheter tube formed of a first material having a first durometer and obtaining a second section of the catheter tube formed of a second material having second durometer less than the first durometer. The method also includes a flaring step of flaring a proximal-end portion of the first section of the catheter tube to form a flared proximal-end portion of the first section of the catheter tube. The method also includes an inserting step of inserting a tapered distal-end portion of the second section of the catheter tube into the flared proximal-end portion of the first section of the catheter tube. The method also includes a welding step of welding the first and second sections of the catheter tube together to form a junction between the first and second sections of the catheter tube.

In some embodiments, the welding step includes heat welding or solvent welding.

In some embodiments, the method further includes a tapering step of tapering a non-tapered distal-end portion of the second section of the catheter tube to form the tapered distal-end portion of the second section of the catheter tube.

In some embodiments, the method further includes a necking-down step of necking down the catheter tube to form a necked-down section about the junction. The necked-down section is configured to provide a smooth transition between the first and second sections of the catheter tube.

Also disclosed herein is a method of a RICC including, in some embodiments, an insertion site-creating step of creating an insertion site with a needle to access a vasculature of a patient; an inserting step of inserting a distal-end portion of a catheter tube of the RICC into the insertion site over the needle; and an advancing step of advancing the distal-end portion of the catheter tube through the vasculature of the patient without use of a Seldinger technique.

In some embodiments, the method further includes a withdrawing step of withdrawing the needle from the RICC after the insertion site-creating step.

In some embodiments, the insertion site is at a right subclavian vein or a right internal jugular vein.

In some embodiments, the advancing step includes advancing the distal-end portion of the catheter tube through the right subclavian vein or the right internal jugular vein, a right brachiocephalic vein, and into a superior vena cava.

Also disclosed herein is a RICC including, in some embodiments, a catheter tube including a first section having a single lumen in a distal-end portion of the catheter tube, a second section having a pair of lumens in the distal-end portion of the catheter tube proximal of the first section, and a junction between the first and second sections of the catheter tube in which the pair of lumens transitions into the single lumen. The first section of the catheter tube is formed of a first material having a first durometer. The second section of the catheter tube is formed of a second material having a second durometer less than the first durometer. The first and second sections of the catheter tube have a column strength sufficient to prevent buckling of the catheter tube when inserted into an insertion site and advanced through a vasculature of a patient.

Disclosed herein is a RICC including, in some embodiments, a catheter tube including a first section in a distal-end portion of the catheter tube, a second section in the distal-end portion of the catheter tube proximal of the first section, and a junction between the first and second sections of the catheter tube. The first and second sections of the catheter tube are formed of a same material or different materials having substantially equal durometers provided the first and second sections of the catheter tube have a column strength sufficient to prevent buckling of the catheter tube when inserted into an insertion site and advanced through a vasculature of a patient.

These and other features of the concepts provided herein will become more apparent to those of skill in the art in view of the accompanying drawings and following description, which describe particular embodiments of such concepts in greater detail.

DRAWINGS

FIG. 1A illustrates a distal-end portion of a first RICC in accordance with some embodiments.

FIG. 1B illustrates a cross section of the distal-end portion of the first RICC of FIG. 1A.

FIG. 2 illustrates a cross section of a second RICC in accordance with some embodiments.

FIG. 3 illustrates a cross section of a third RICC in accordance with some embodiments.

FIG. 6A illustrates a distal-end portion of a fourth RICC in accordance with some embodiments.

FIG. 6B illustrates a cross section of the distal-end portion of the fourth RICC of FIG. 6A.

DESCRIPTION

Figures 4A, 4B:
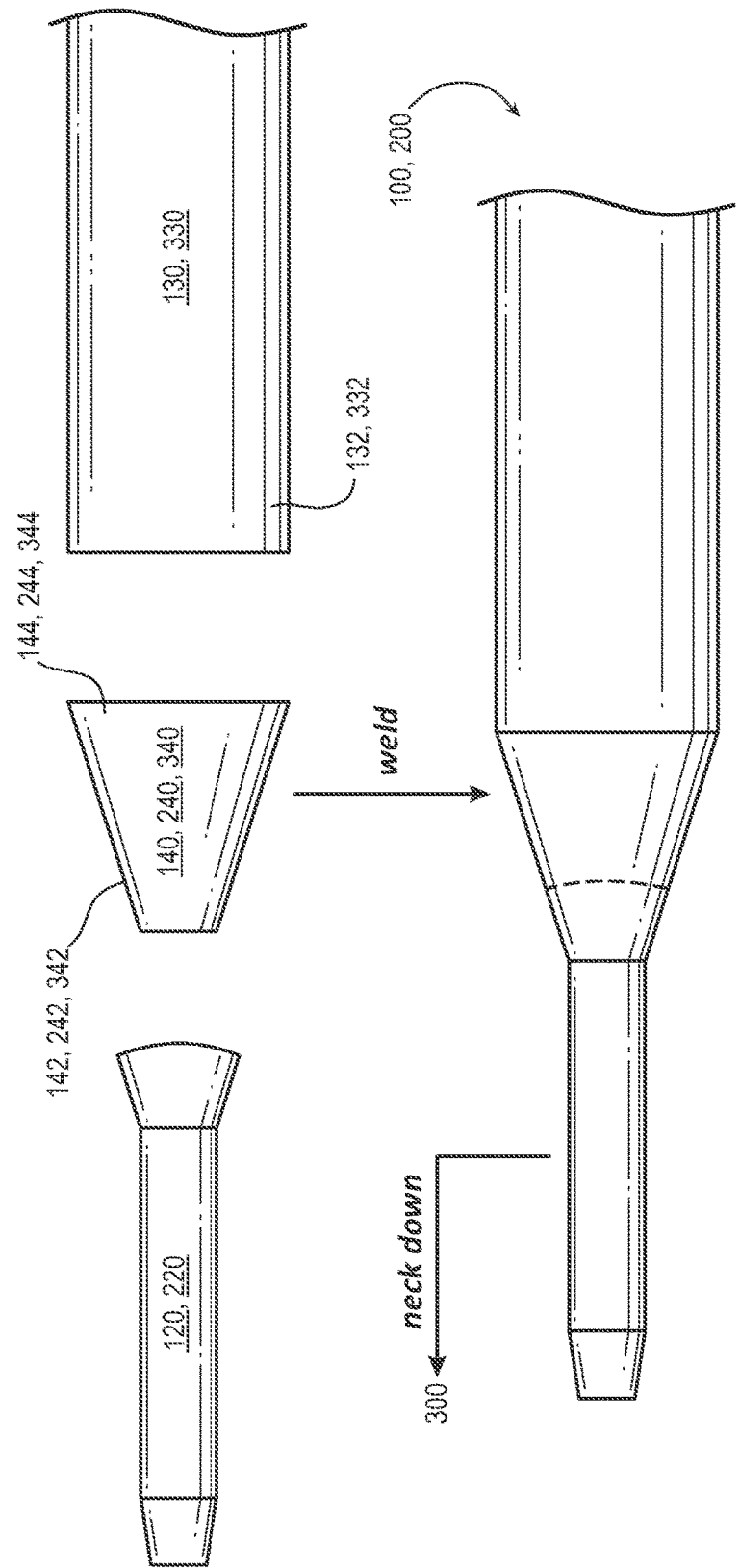
FIG. 4A illustrates part of a method of making at least the first RICC in accordance with some embodiments.
FIG. 4B illustrates another part of the method of making at least the first RICC in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter into patient and advancing the catheter through a vasculature thereof. Disclosed herein are RICCs and methods thereof that address the foregoing.

Rapidly Inserted Central Catheters

FIG. 1A illustrates a distal-end portion of a RICC 100 in accordance with some embodiments. FIG. 1B illustrates a cross section of the distal-end portion of the RICC 100 of FIG. 1A. FIG. 2 illustrates a cross section of a RICC 200 in accordance with some embodiments. FIG. 3 illustrates a cross section of a RICC 300 in accordance with some embodiments. FIG. 6A illustrates a distal-end portion of a RICC 600 in accordance with some embodiments. FIG. 6B illustrates a cross section of the distal-end portion of the RICC 600 of FIG. 6A.

As shown, the RICC 100 includes a catheter tube 110 including a first section 120 in the distal-end portion of the catheter tube 110, a second section 130 in the distal-end portion of the catheter tube 110 proximal of the first section 120, and a junction 140 between the first section 120 and second section 130 of the catheter tube 110. Likewise, the RICC 200 includes a catheter tube 210 including a first section 220 in the distal-end portion of the catheter tube 210, the second section 130 in the distal-end portion of the catheter tube 210 proximal of the first section 220, and a junction 240 between the first section 220 and second section 130 of the catheter tube 210. Further likewise, the RICC 300 includes a catheter tube 310 including the first section 220 in the distal-end portion of the catheter tube 310, a second section 330 in the distal-end portion of the catheter tube 310 proximal of the first section 220, and a junction 340 between the first section 220 and second section 330 of the catheter tube 310. Even further likewise, the RICC 600 includes a catheter tube 610 including a first section 620 in the distal-end portion of the catheter tube 610, the second section 130 in the distal-end portion of the catheter tube 610 proximal of the first section 620, and the junction 140 between the first section 620 and second section 130 of the catheter tube 610. Together, the first section 120, 220, or 620 of the catheter tube 110, 210, 310, or 610, the second section 130 or 330 of the catheter tube 110, 210, 310, or 610 and the junction 140, 240, or 340 have a column strength sufficient to prevent buckling of the catheter tube 110, 210, 310, or 610 when inserted into an insertion site and advanced through a vasculature of a patient. While the RICC 100, 200, 300, and 600 have the foregoing sections, it should be understood other sections and configurations thereof are possible.

While only a single lumen 112 is shown for the RICC 100, 200, 300, or 600, the RICC 100, 200, 300, or 600 is not limited to being a monoluminal catheter. Indeed, the RICC 100, 200, 300, or 600 can alternatively be a diluminal catheter, a triluminal catheter, a tetraluminal catheter, etc. A number of lumens 112 in one portion of the RICC 100, 200, 300, or 600 can also transition into a fewer number of lumens 112 in another portion of the RICC 100, 200, 300, or 600. For example, a pair of lumens 112 in the second section 130 of the catheter tube 110 of the RICC 100 can transition into the single 112 lumen in the first section 120 of the catheter tube 110.

The first section 120 or 220 of the catheter tube 110, 210, or 310 includes a flared proximal-end portion 122 or 222 and a tip 124 of the first section 120 or 220 of the catheter tube 110, 210, or 310 that doubles as the tip 124 of the catheter tube 110, 210, or 310. The flared proximal-end portions 122 or 222 can differ with respect to degree of flare with the flared proximal-end portion 122 of the first section 110 having a greater degree of flare than the flared proximal-end portion 222 of the first section 220 of either the second catheter tube 210 or the third catheter tube 310. While the first section 620 of the catheter tube 610 likewise includes the tip 124 that doubles as the tip 124 of the catheter tube 610, the first section 620 of the catheter tube 610 does not include a flared proximal-end portion like the flared proximal-end portion 122 or 222 of the first section 120 or 220 of the catheter tube 110, 210, or 310. Instead, a proximal-end portion 622 of the first section 620 of the catheter tube 610 continues with a same outer diameter as a distal-end portion of the first section 620 of the catheter tube 610 proximal of the tip 124.

The first section 120, 220, or 620 of the catheter tube 110, 210, 310, or 610 is formed of a first material having a first durometer. The first material can be polytetrafluoroethylene, polypropylene, or polyurethane, but the first material is not limited to the foregoing polymers. Polyurethane is advantageous in that the first section 120, 220, or 620 of the catheter tube 110, 210, 310, or 610 can be relatively rigid at room-temperature but become more flexible in vivo at body temperature, which reduces irritation to vessel walls and phlebitis.

The second section 130 or 330 of the catheter tube 110, 210, 310, or 610 includes a distal-end portion 132, 232, or 332 as best seen in FIG. 4B.

The second section 130 or 330 of the catheter tube 110, 210, 310, or 610 is formed of a second material having a second durometer less than the first durometer of the first material. The first durometer and the second durometer can be on different scales (e.g., Type A or Type D), so the second durometer might not be numerically less than the first durometer. That said, the hardness of the second material can still be less than the hardness of the first material as the different scales—each of which ranges from 0 to 100—are designed for characterizing different materials in groups of the materials having a like hardness. The second material can be polyvinyl chloride, polyethylene, polyurethane, or silicone, but the first material is not limited to the foregoing polymers. Polyurethane is advantageous in that can be less thrombogenic than some other polymers.

Notwithstanding the foregoing, the first section 120, 220, or 620 and the second section 130 or 330 of the catheter tube 110, 210, 310, or 610 can be formed of a same material or different materials having substantially equal durometers provided a column strength of the catheter tube 110, 210, 310, or 610 is sufficient to prevent buckling of the catheter tube 110, 210, 310, or 610 when inserted into an insertion site and advanced through a vasculature of a patient.

The junction 140, 240, or 340 can be a third section of the catheter tube 110, 210, 310, or 610. The junction 140, 240, or 340 includes a tapered distal-end portion 142, 242, or 342 as best seen in FIG. 4B, as well as a proximal-end portion 144, 244, or 344. Each tapered distal-end portion of the tapered distal-end portions 142, 242, and 342 can differ with respect to degree of taper. For example, the tapered distal-end portion 142 of the junction 140 can have a greater degree of taper than the tapered distal-end portion 242 or 342 of the junction 240 or 340.

The junction 140, 240, or 340 is formed of a third material having a third durometer between the first durometer of the first material of the first section 120, 220, or 620 of the catheter tube 110, 210, 310, or 610 and the second durometer of the second material of the second section 130 or 330 of the catheter tube 110, 210, 310, or 610. Like that set forth above, such durometers can be on different scales (e.g., Type A or Type D), so the third durometer might not be numerically between the first durometer and the second durometer. Alternatively, the third material can have a same durometer as the first material of the first section 120, 220, or 620 of the catheter tube 110, 210, 310, or 610 or the second material of the second section 130 or 330 of the catheter tube 110, 210, 310, or 610.

The tapered distal-end portion 142, 242, or 342 of the junction 140, 240, or 340 sits at least partially within the flared proximal-end portion 122 or 222 of the first section 120 or 220 of the catheter tube 110, 210, or 310. With respect to the catheter tube 610, however, the tapered distal-end portion 142 of the junction 140 abuts the proximal-end portion 622 of the first section 620 of the catheter tube 610. The proximal-end portion 144, 244, or 344 of the junction 140, 240, or 340 abuts the distal-end portion 132 or 332 of the second section 130 or 330 of the catheter tube 110, 210, 310, or 610. Each section of the first section 120, 220, or 620 and second section 130 or 330 of the catheter tube 110, 210, 310, or 610 is independently welded to the junction 140, 240, or 340 in a heat weld or a solvent weld. If one type of welding is used, the first section 120, 220, or 620 and second section 130 or 330 of the catheter tube 110, 210, 310, or 610 can be welded to the junction 140, 240, or 340 in one heat-welding or a solvent-welding step. The flared proximal-end portion 122 of the first section 120 of the catheter tube 110 is exposed, whereas the flared proximal-end portion 222 of the first section 220 of the catheter tube 210 or 310 is concealed by an overlying portion of the junction 240 or 340 for a smoother transition. For an even smoother transition, both the second section 330 of the catheter tube 310 and the junction 340 can be necked-down in a combined necked down section about the junction 340.

Figure 5A:
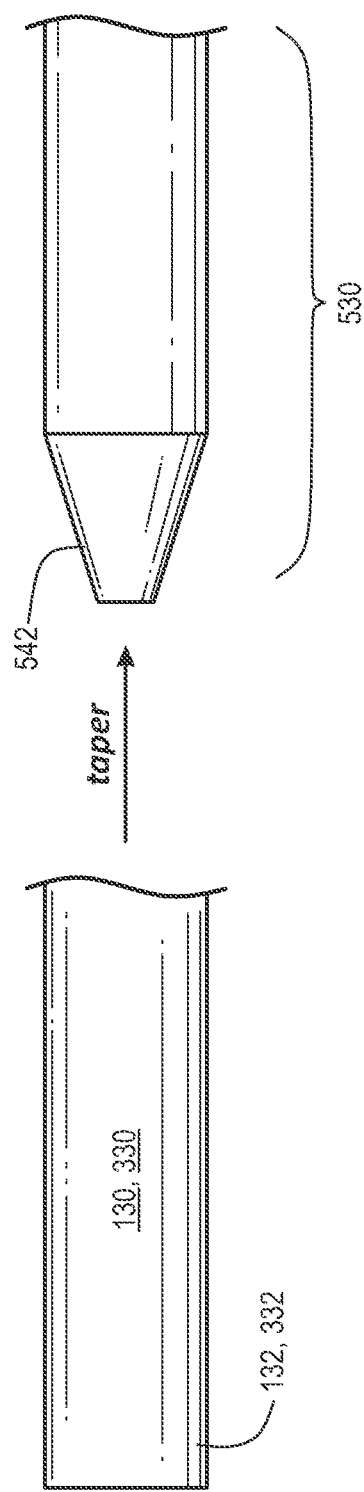
FIG. 5A illustrates part of a method of making at least an alternative of the first RICC in accordance with some embodiments.

As an alternative to the foregoing, the second section 130 or 330 of the catheter tube 110, 210, 310, or 610 includes the junction 140, 240, or 340 or third section of the catheter tube 110, 210, 310, or 610. That is, the third section of the catheter tube 110, 210, 310, or 610 is not formed separately from the second section 130 or 330 of the catheter tube 110, 210, 310, or 610 and welded thereto—but integrally with the second section 130 or 330 of the catheter tube 110, 210, 310, or 610 as shown in FIG. 5A for a second section 530. Like that set forth above for the junction 140, 240, or 340, the second section 530 includes a tapered distal-end portion 542. The tapered distal-end portion 542 can differ with respect to degree of taper. For example, the tapered distal-end portion 542 of the second section 530 can have a greater degree of taper for the catheter tube 110 or 610 than for either catheter tube of the catheter tubes 210 and 310.

The tapered distal-end portion 542 of the second section 530 of the catheter tube 110, 210, or 310 sits at least partially within the flared proximal-end portion 122 or 222 of the first section 120 or 220 of the catheter tube 110, 210, or 310 or abuts the proximal-end portion 622 of the first section 620 of the catheter tube 610. The first section 120, 220, or 620 and second section 530 of the catheter tube 110, 210, 310, or 610 are welded together in a heat weld or a solvent weld. The flared proximal-end portion 122 of the first section 120 of the catheter tube 120 is exposed, whereas the flared proximal-end portion 222 of the first section 220 of the catheter tube 210 or 310 is concealed by an overlying portion of the second section 530 of the catheter tube 210 or 310 for a smoother transition. For an even smoother transition, the second section 530 of the catheter tube 310 can be necked-down in a necked down section.

Methods

Figure 7:
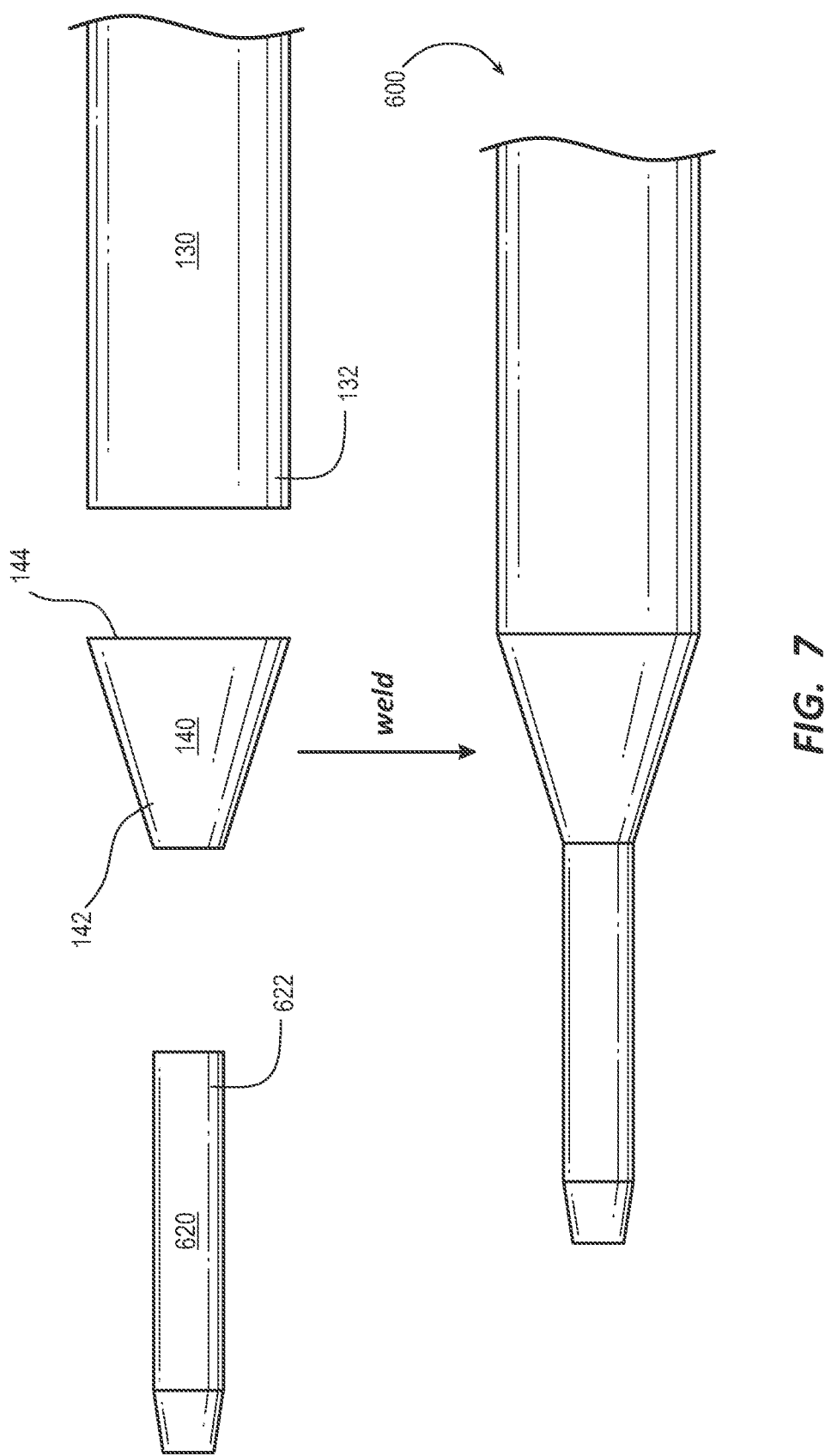
FIG. 7 illustrates another part of the method of making at least the fourth RICC in accordance with some embodiments.

FIGS. 4A and 4B illustrate a method of making at least the RICC 100 in accordance with some embodiments. Indeed, the method shown in FIGS. 4A and 4B is also applicable to the RICC 200 and 300. FIG. 7 illustrates a method of making at least the RICC 600 accordance with some embodiments. The method of making the RICC 600 is analogous to that shown in FIG. 4B for the RICC 100 albeit without aspects of the method directed to the flared proximal-end portion 122 of the first section 120 of the catheter tube 110. For expository expediency, the method of FIGS. 4A and 4B will be primarily described with reference to making the RICC 100. Only where the method of making the RICC 200, 300, or 600 appreciably diverges from that of the RICC 100 will the method of FIGS. 4A and 4B be described with reference to the RICC 200 or 300 or the method of FIG. 7 be described with reference to the RICC 600.

The method of making the RICC 100 includes obtaining steps of obtaining each section of the first section 120, the second section 130, and the junction or third section 140 of the catheter tube 110. Again, the first section 120 of the catheter tube 110 is formed of a first material having a first durometer, the second section 130 of the catheter tube 110 is formed of a second material having a second durometer, and the third section 140 of the catheter tube 110 is formed of a third material having a third durometer between the first and second durometers. Such materials having such durometers make use of different melting temperatures and promote welds between the different sections 120, 130, and 140 of the catheter tube 110 sufficient for using the RICC 100.

The method also includes a flaring step of flaring a proximal-end portion of a nascent first section 424 of the catheter tube 110 to form the first section 120 of the catheter tube 110 with the flared proximal-end portion 122. Notably, the first section 620 of the catheter tube 610 does not include a flared proximal-end portion like the flared proximal-end portion 122 of the first section 120 of the catheter tube 110. Therefore, the method of making the RICC 600 need not include the foregoing flaring step.

The method also includes an inserting step of inserting the tapered distal-end portion 142 of the third section 140 of the catheter tube 110 into the flared proximal-end portion 122 of the first section 120 of the catheter tube 110. Notably, the first section 620 of the catheter tube 610 does not include a flared proximal-end portion like the flared proximal-end portion 122 of the first section 120 of the catheter tube 110. Therefore, the method of making the RICC 600 need not include the foregoing inserting step. Instead, the method of making the RICC 600 includes an abutting step of abutting the tapered distal-end portion 142 of the third section 140 of the catheter tube 610 into the proximal-end portion 622 of the first section 620 of the catheter tube 610.

The method also includes an abutting step of abutting the distal-end portion 132 of the second section 130 of the catheter tube 110 and the proximal-end portion 144 of the third section 140 of the catheter tube 110.

The method also includes welding steps of welding the first, second, and third sections of the catheter tube 110 together to form the junction 140 of the third material between the first section 120 and second section 130 of the catheter tube 110.

The welding step of welding the second section 130 and third section 140 of the catheter tube occurs before the inserting and welding steps of inserting the tapered distal-end portion 142 of the third section 140 of the catheter tube 110 into the flared proximal-end portion 122 of the first section 120 of the catheter tube 110 and welding the first section 120 and third section 140 of the catheter tube 110 together. With respect to the method of making the RICC 600, the welding step of welding the second section 130 and third section 140 of the catheter tube occurs before the abutting and welding steps of abutting the tapered distal-end portion 142 of the third section 140 of the catheter tube 610 and the proximal-end portion 622 of the first section 620 of the catheter tube 610 and welding the first section 620 and third section 140 of the catheter tube 610 together. Each welding step of the welding steps is independently heat welding (e.g., radiofrequency ["RF"] welding) or solvent welding.

Flaring the proximal-end portion of the nascent first section 424 of the catheter tube 110 to form the flared proximal-end portion 122 of the first section 120 of the catheter tube 110 and inserting the tapered distal-end portion 142 of the third section 140 of the catheter tube 110 into the flared proximal-end portion 122 of the first section 120 of the catheter tube 110 makes it possible to place an RF-welding element a short distance from a start of the flared proximal-end portion 122 of the first section 120 of the catheter tube 110. This reduces a risk of causing a defect or a weak spot in the catheter tube 110. The RF-welding element would touch off a short distance distal of portion 121 and a short distance proximal of the portion 121 where the flared proximal-end portion 122 of the first section 120 of the catheter tube 110 begins so as to avoid too much heat exposure to the thin wall of the first section 120 of the catheter tube 110.

The method further includes a tapering step of tapering a non-tapered distal-end portion of the third section 140 of the catheter tube 110 to form the tapered distal-end portion 142 of the third section 140 of the catheter tube 110.

For at least the RICC 300, the method further includes a necking-down step of necking down the catheter tube 310 to form a necked-down section about the junction 340. The necked-down section is configured to provide a smooth transition between the first, second, and third sections of the catheter tube 310.

Figure 5B:
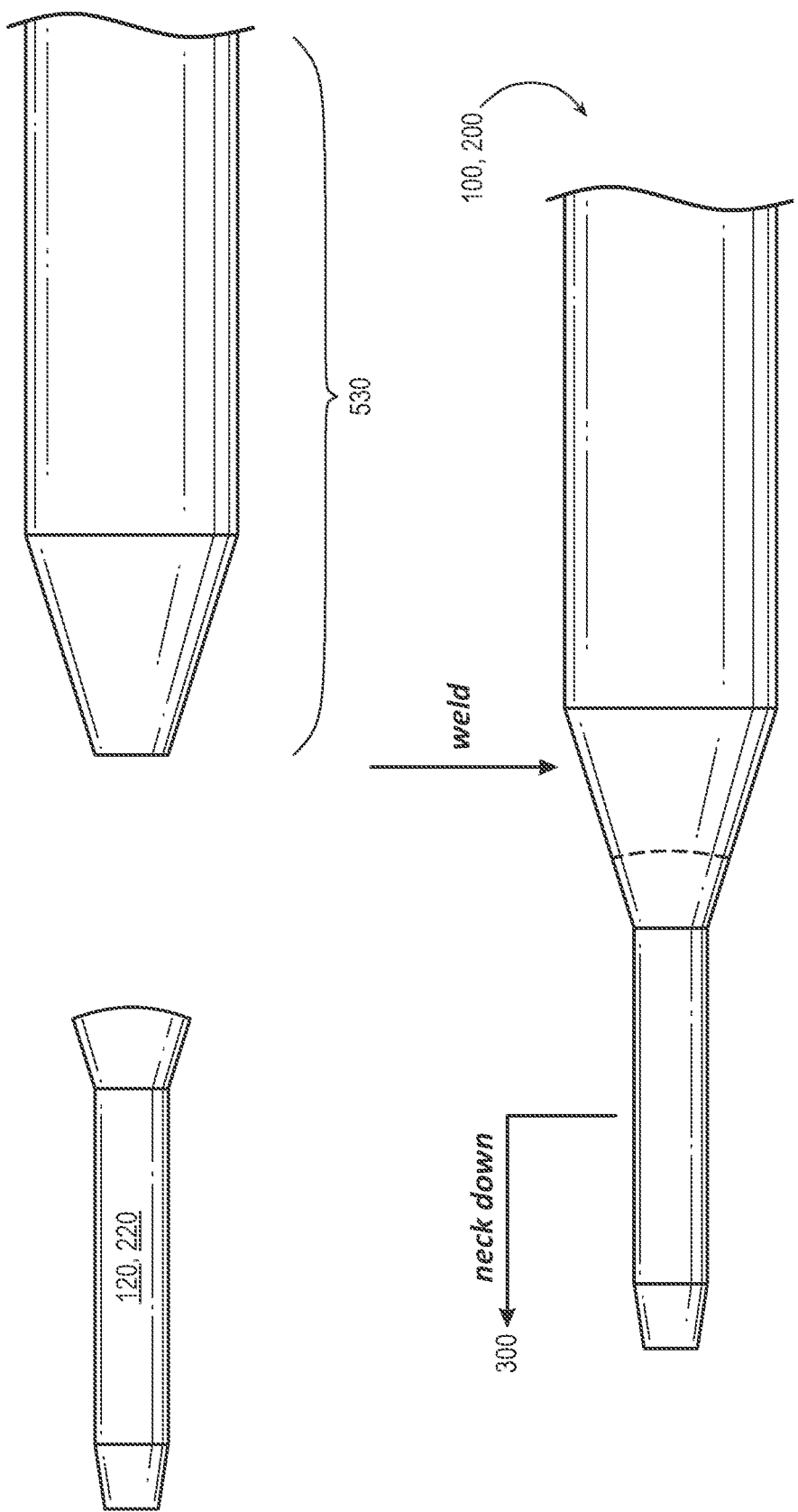
FIG. 5B illustrates another part of the method of making at least the alternative of the second RICC in accordance with some embodiments.

FIGS. 5A and 5B illustrate a method of making the alternative of the RICC 100 in accordance with some embodiments.

The method of making the alternative to the RICC 100 includes obtaining steps of obtaining the first section 120 of the catheter tube 110 formed of a first material having a first durometer and the second section 530 of the catheter tube 110 formed of a second material having second durometer less than the first durometer. The method also includes a flaring step of flaring the nascent first section 424 of the catheter tube 110 as shown in FIG. 4B to form the flared proximal-end portion 122 of the first section 120 of the catheter tube 110. The method also includes an inserting step of inserting the tapered distal-end portion 542 of the second section 530 of the catheter tube 110 into the flared proximal-end portion 122 of the first section 120 of the catheter tube 110. The method also includes a welding step of heat or solvent welding the first section 120 and second section 530 of the catheter tube 110 together to form a junction therebetween.

The method further includes a tapering step of tapering a non-tapered distal-end portion 132 of the second section 130 of the catheter tube 110 to form the tapered distal-end portion 542 of the second section 530 of the catheter tube 110. Forming the tapered distal-end portion 542 of the second section 530 of the catheter tube 110 can be accomplished by removing some material from the non-tapered distal-end portion 132 of the second section 130 of the catheter tube 110 or melting or dissolving some of the material of the non-tapered distal-end portion 132 of the second section 130 of the catheter tube 110 during the welding step.

For at least the RICC 300, the method further includes a necking-down step of necking down the catheter tube 310 to form a necked-down section about the junction between the first section 120 and second section 530 of the catheter tube 110. The necked-down section is configured to provide a smooth transition between the first section 220 and second section 530 of the catheter tube 310.

The method of making each RICC of the RICCs 100, 200, and 300 further includes a mandrel-mounting step of mounting the sections used in making the RICCs 100, 200, and 300 on mandrels to keep lumens thereof from collapsing during the more welding steps.

A method of the RICC 100 includes an insertion site-creating step of creating an insertion site with a needle to access a vasculature of a patient; an inserting step of inserting the distal-end portion of the catheter tube 110 of the RICC 100 into the insertion site over the needle; and an advancing step of advancing the distal-end portion of the catheter tube 110 through the vasculature of the patient without use of a Seldinger technique. A smaller outer diameter of the first section 120 of the RICC 100 facilitates the inserting step, which requires pushing through at least skin tissue. In addition, the transition between the first section 120 and second section 130 eliminates snagging on at least the skin tissue making it possible to insert the RICC 100 like a peripheral intravenous ("IV") catheter.

The method further includes a withdrawing step of withdrawing the needle from the RICC 100 after the insertion site-creating step.

The insertion site is at a right subclavian vein or a right internal jugular vein.

The advancing step includes advancing the distal-end portion of the catheter tube 110 through the right subclavian vein or the right internal jugular vein, a right brachiocephalic vein, and into a superior vena cava.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly inserted central catheter ("RICC"), comprising:
    a first section of a catheter tube consisting of a first material having a first durometer, the first section in a distal-end portion of the catheter tube;
    a second section of the catheter tube consisting of a second material having a second durometer less than the first durometer, the second section in the distal-end portion of the catheter tube proximal of the first section, the first section and the second section of the catheter tube having a column strength sufficient to prevent buckling of the catheter tube when inserted into an insertion site and advanced through a vasculature of a patient; and
    a junction as a third section of the catheter tube including a third material having a third durometer between the first durometer and the second durometer, the junction located between the first section and the second section of the catheter tube and the junction including a tapered distal-end portion, the first section of the catheter tube including a flared proximal-end portion, and the tapered distal-end portion of the junction sitting within the flared proximal-end portion of the first section of the catheter tube.

2. The RICC of claim 1, wherein the junction includes a proximal-end portion, the second section of the catheter tube includes the distal-end portion, and the proximal-end portion of the junction abuts the distal-end portion of the second section of the catheter tube.

3. The RICC of claim 1, wherein the first section and the second section of the catheter tube are welded to the junction in a heat weld.

4. The RICC of claim 1, wherein the first section and the second section of the catheter tube are welded to the junction in a solvent weld.

5. The RICC of claim 1, wherein the RICC includes a necked-down section about the junction, the necked-down section configured to provide a smooth transition between the first section and the second section of the catheter tube.

6. The RICC of claim 1, wherein the first section of the catheter tube is polytetrafluoroethylene, polypropylene, or polyurethane.

7. The RICC of claim 1, wherein the second section of the catheter tube is polyvinyl chloride, polyethylene, polyurethane, or silicone.

8. The RICC of claim 1, wherein the first section of the catheter tube has a single lumen, the second section of the catheter tube has a pair of lumens, and the pair of lumens transitions into the single lumen in the junction.

9. A method of making a rapidly inserted central catheter ("RICC"), comprising:
    obtaining a first section of a catheter tube consisting of a first material having a first durometer, a second section of the catheter tube consisting of a second material having a second durometer, and a third section of the catheter tube including a third material having a third durometer between the first durometer and the second durometer;
    flaring a proximal-end portion of the first section of the catheter tube to form a flared proximal-end portion of the first section of the catheter tube;
    inserting a tapered distal-end portion of the third section of the catheter tube into the flared proximal-end portion of the first section of the catheter tube;
    abutting a distal-end portion of the second section of the catheter tube and the proximal-end portion of the third section of the catheter tube; and
    welding the first, second, and third sections of the catheter tube together to form a junction of the third material between the first section and the second section of the catheter tube.

10. The method of claim 9, wherein welding the second section and the third section of the catheter tube occurs prior to inserting the tapered distal-end portion of the third section of the catheter tube into the flared proximal- end portion of the first section of the catheter tube and welding the first section and the third section of the catheter tube together.

11. The method of claim 9, wherein welding is independently heat welding or solvent welding.

12. The method of claim 9, further comprising tapering a non-tapered distal-end portion of the third section of the catheter tube to form the tapered distal-end portion of the third section of the catheter tube.

13. The method of claim 9, further comprising necking down the catheter tube to form a necked-down section about the junction, the necked-down section configured to provide a smooth transition between the first, second, and third sections of the catheter tube.

14. A method of making a rapidly inserted central catheter ("RICC"), comprising:
    obtaining a first section of a catheter tube consisting of a first material having a first durometer and a second section of the catheter tube consisting of a second material having second durometer less than the first durometer;
    flaring a proximal-end portion of the first section of the catheter tube to form a flared proximal-end portion of the first section of the catheter tube;
    inserting a tapered distal-end portion of the second section of the catheter tube into the flared proximal-end portion of the first section of the catheter tube; and
    welding the first section and the second section of the catheter tube together to form a junction between the first section and the second section of the catheter tube.

15. The method of claim 14, wherein welding is heat welding or solvent welding.

16. The method of claim 14, further comprising tapering a non-tapered distal-end portion of the second section of the catheter tube to form the tapered distal-end portion of the second section of the catheter tube.

17. The method of claim 14, further comprising necking down the catheter tube to form a necked-down section about the junction, the necked-down section configured to provide a smooth transition between the first section and the second section of the catheter tube.

18. A rapidly inserted central catheter ("RICC"), comprising:
   a first section of a catheter tube consisting of a first material having a first durometer, the first section in a distal-end portion of the catheter tube;
   a second section of the catheter tube consisting of a second material having a second durometer less than the first durometer, the second section in the distal-end portion of the catheter tube proximal of the first section, the first section and the second section of the catheter tube having a column strength sufficient to prevent buckling of the catheter tube when inserted into an insertion site and advanced through a vasculature of a patient; and
   a junction between the first section and the second section of the catheter tube, the first section of the catheter tube including a flared proximal-end portion, the second section of the catheter tube including a tapered distal-end portion, and the tapered distal-end portion of the second section of the catheter tube sitting within the flared proximal-end portion of the first section of the catheter tube.

19. The RICC of claim 18, wherein the RICC includes a necked-down section about the junction, the necked-down section configured to provide a smooth transition between the first section and the second section of the catheter tube.

20. The RICC of claim 18, wherein the first section of the catheter tube is polytetrafluoroethylene, polypropylene, or polyurethane.

21. The RICC of claim 18, wherein the second section of the catheter tube is polyvinyl chloride, polyethylene, polyurethane, or silicone.

22. The RICC of claim 18, wherein the first section of the catheter tube has a single lumen, the second section of the catheter tube has a pair of lumens, and the pair of lumens transitions into the single lumen in the junction.

23. The RICC of claim 18, wherein the first section and the second section of the catheter tube are welded together in a heat weld, thereby forming the junction between the first section and the second section of the catheter tube.

24. The RICC of claim 18, wherein the first section and the second section of the catheter tube are welded together in a solvent weld, thereby forming the junction between the first section and the second section of the catheter tube.

* * * * *